United States Patent
Henderson

(10) Patent No.: US 8,969,808 B2
(45) Date of Patent: Mar. 3, 2015

(54) NON-DISPERSIVE INFRARED SENSOR WITH A REFLECTIVE DIFFUSER

(75) Inventor: David Benjamin Henderson, Goleta, CA (US)

(73) Assignee: Amphenol Thermometrics, Inc., St. Marys, PA (US)

(*) Notice: Subject to any disclaimer, the term of this patent is extended or adjusted under 35 U.S.C. 154(b) by 0 days.

(21) Appl. No.: 13/526,589

(22) Filed: Jun. 19, 2012

(65) Prior Publication Data
US 2013/0334423 A1 Dec. 19, 2013

(51) Int. Cl.
*G01J 5/02* (2006.01)
*G01J 5/00* (2006.01)

(52) U.S. Cl.
USPC ............ 250/343; 250/338.1; 250/338.3; 250/339.11; 250/339.13; 250/341.8

(58) Field of Classification Search
USPC .......................................... 250/343
See application file for complete search history.

(56) References Cited

U.S. PATENT DOCUMENTS

| | | |
|---|---|---|
| 5,341,214 A | 8/1994 | Wong |
| 5,834,777 A | 11/1998 | Wong |
| 5,874,737 A | 2/1999 | Bytyn et al. |
| 6,410,918 B1 * | 6/2002 | Kouznetsov ............ 250/343 |
| 6,469,303 B1 * | 10/2002 | Sun et al. ............ 250/343 |
| 7,541,587 B2 | 6/2009 | Cutler et al. |
| 2006/0256415 A1 | 11/2006 | Holmes et al. |
| 2007/0017458 A1 | 1/2007 | Frodl et al. |
| 2009/0039267 A1 | 2/2009 | Arndt et al. |
| 2010/0078563 A1 | 4/2010 | Haveri et al. |

FOREIGN PATENT DOCUMENTS

EP 0794423 9/1997

OTHER PUBLICATIONS

Hodgkinson et al., Gas cells for tunable diode laser absorption spectroscopy employing optical diffusers. Part 1: Single and dual pass cells, 2009, 7th International Conference on Tunable Diode Laser Spectroscopy, pp. 1-25, online at https://dspace.lib.cranfield.ac.uk/bitstream/1826/4763/3/Gas_cells_for_tunable_diode_laser_absorption-pt1.pdf.*
European Search Report dated Jan. 8, 2014 issue in European Patent Application No. 13172490.8.
Electroless nickel immersion gold, Wikipedia, Apr. 2, 2012, p. 1.

* cited by examiner

*Primary Examiner* — David Porta
*Assistant Examiner* — Jeremy S Valentiner
(74) *Attorney, Agent, or Firm* — Blank Rome LLP

(57) ABSTRACT

The present application provides a non-dispersive infrared gas sensor. The non-dispersive infrared gas sensor may include an infrared source, an infrared detector, and a waveguide extending about the infrared source and the infrared detector. The waveguide may include a reflective diffuser thereon.

19 Claims, 3 Drawing Sheets

US 8,969,808 B2

NON-DISPERSIVE INFRARED SENSOR WITH A REFLECTIVE DIFFUSER

TECHNICAL FIELD

The present disclosure relates generally to a non-dispersive infrared gas sensor and more particularly relates to a non-dispersive infrared gas sensor with a reflective diffuser therein to promote scattering so as to reduce overall mechanical sensitivity.

BACKGROUND OF THE INVENTION

Gas sensors such as a non-dispersive infrared ("NDIR") gas sensor may measure gas concentrations based upon infrared absorption. Specifically, NDIR gas sensors measure the gas concentrations based on unique absorption characteristics specific to each gas at certain wavelengths. In other words, different gases have clearly defined absorption characteristics. The NDIR gas sensors may include an infrared source and an infrared detector. The infrared source may be modulated and the measured signal may be correlated to the gas concentrations. A waveguide may be used as the gas sample chamber between the source and the detector. The internal surface of the waveguide typically is smooth and reflective so as to minimize the scattering of the infrared light therein. The waveguide surface thus may provide near specular reflections so as to maximize the signal received at the detector.

Although the smooth surface providing nearly specular reflections may minimize scattering and maximize the signal, a gas sensor using such a surface also may be sensitive to mechanical changes. For example, temperature changes may have an impact on the components and, hence, the reliability of the signal. As a result, known attempts to increase overall gas sensor stability have involved the use of precision components and/or burn in periods so as to stabilize the electronics therein. These techniques, however, generally may be expensive and/or time consuming.

There is thus a desire for an improved gas sensor such as a NDIR gas sensor. Such an improved NDIR gas sensor may provide overall mechanical stability for a more homogeneous signal without requiring the use of expensive components or modifications.

SUMMARY OF THE INVENTION

The present application and the resultant patent thus provide a non-dispersive infrared gas sensor. The non-dispersive infrared gas sensor may include an infrared source, an infrared detector, and a waveguide extending about the infrared source and the infrared detector. The waveguide may include a reflective diffuser thereon.

The present application and the resultant patent further provide a method of measuring a concentration of a gas in a chamber. The method may include the steps of pulsing an infrared signal into the chamber, scattering the infrared signal off of a reflective diffuser, receiving the scattered infrared signal at an infrared detector, and determining the intensity of the scattered infrared signal.

The present application and the resultant patent further provide a non-dispersive infrared gas sensor. The non-dispersive infrared gas sensor may include an infrared source, an infrared detector, and a waveguide extending about the infrared source and the infrared detector. The waveguide may include a reflective diffuser with a textured surface and a reflective coating thereon.

These and other features and improvements of the present application and the resultant patent will become apparent to one of ordinary skill in the art upon review of the following detailed description when taken in conjunction with the several drawings and the appended claims.

DETAILED DESCRIPTION

Figure 1:
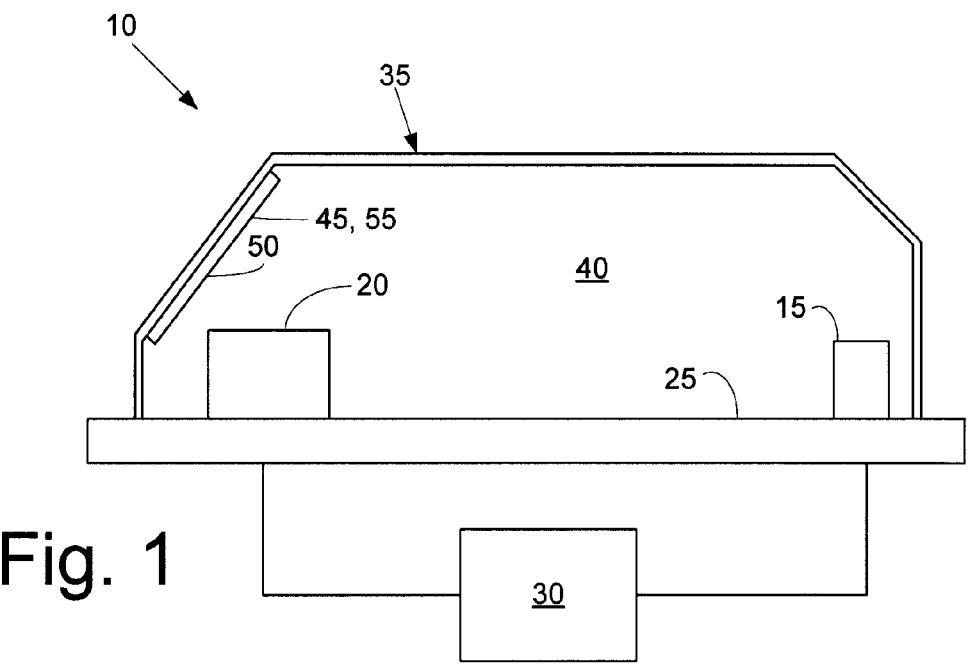
FIG. 1 is a schematic diagram of an NDIR gas sensor.

Referring now to the drawings, in which like numerals refer to like elements throughout the several views, FIG. 1 shows a typical NDIR gas sensor. Generally described, the NDIR gas sensor 10 may include an infrared source 15 and an infrared detector 20. More than one infrared detector 20 may be used. The infrared source 15 and the infrared detector 20 may be positioned on a printed circuit board 25. The infrared source 15 and the infrared detector 20 may be in communication via a microprocessor 30. Various types of amplifiers, filters, and other components also may be used.

The NDIR sensor 10 may be enclosed by a waveguide 35. The waveguide 35 may define a chamber 40 extending from and enclosing in part the infrared source 15 to the infrared detector 20. The waveguide 35 may include one or more internal reflective surfaces 45. The reflective surfaces 45 typically may be smooth and may provide near specular reflection so as to minimize scattering of the light therein. The waveguide 35 may be made from thermoplastic, metal, rubber, composite materials, and the like. If the waveguide 35 is made out of thermoplastics, for example, the injection mold for the waveguide 35 may be highly polished about the reflective surfaces 45. The reflective surfaces 45 then may receive a plate or coating 50. The plate or coating 50 may be a metal surface so as to produce a near specular reflective surface 55. Specifically, such a near specular reflective surface 55 may maximize the signal received at the infrared detector 20 by limiting scattering.

As described above, the infrared source 15 may pulse an infrared beam within the chamber 40. The beam may reflect off of the reflective surfaces 45 of the waveguide 35 and may be received by the infrared detector 20. The gas within the chamber 40 absorbs radiation of a known wavelength and this absorption is a measure of the concentration of the gas. Different gases have clearly defined absorption characteristics. The infrared detector 20 thus delivers a signal proportional to the gas concentration to the microprocessor 30. These signals then may be averaged. Other components and other configurations may be used.

Figure 2:
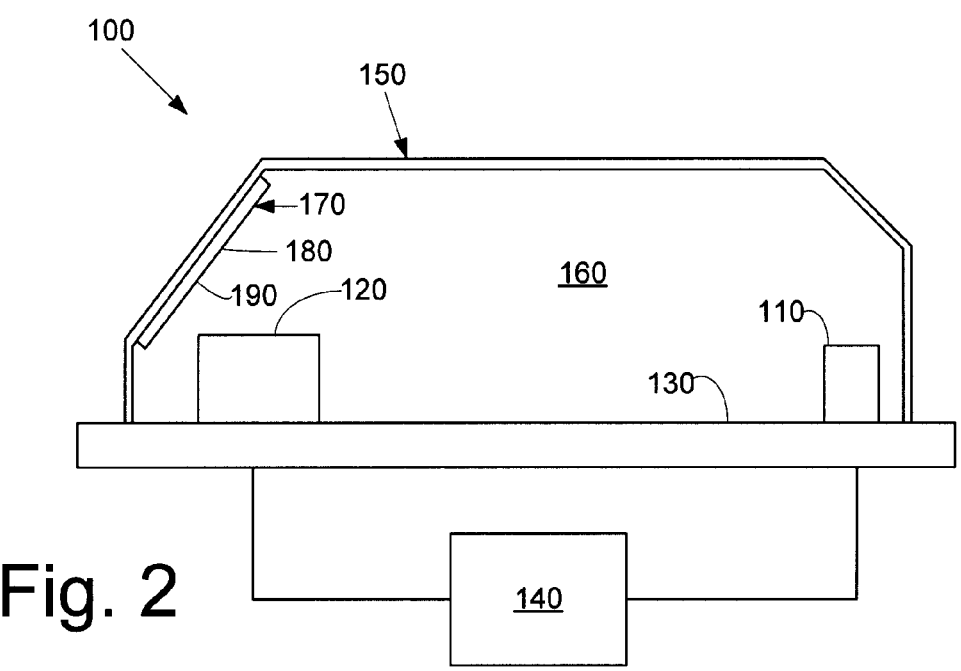
FIG. 2 is a schematic diagram of an NDIR gas sensor as may be described herein.

FIG. 2 shows a NDIR gas sensor 100 as may be described herein. Similar to that described above, the NDIR gas sensor 100 may include an infrared source 110 and an infrared detector 120. More than one infrared detector 120 may be used herein. The infrared source 110 and the infrared detector 120 may be of conventional design. The infrared source 110 and the infrared detector 120 may be positioned about a printed circuit board 130 or other type of mechanical support and/or electronic connection. The infrared source 110 and the infrared detector 120 may be in communication via a microprocessor 140. The microprocessor 140 may be any type of programmable logic device. Various types of filters, amplifiers, and the like also may be used herein. Other components and other configurations may be used herein.

The NDIR gas sensor 100 also may include a waveguide 150. The waveguide 150 may define a chamber 160 therein extending from the infrared source 110 to the infrared detector 120. The waveguide 150 may be made from thermoplastics, metal, rubber, composite materials and the like. The waveguide 150 may have any size, shape, or configuration.

Figure 3:
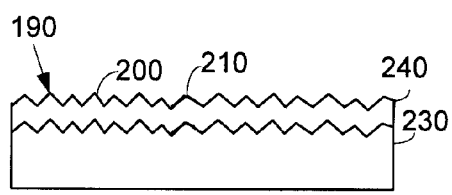
FIG. 3 is a side cross-sectional view of a reflective diffuser as may be used with the NDIR sensor of FIG. 2.
Figure 4:
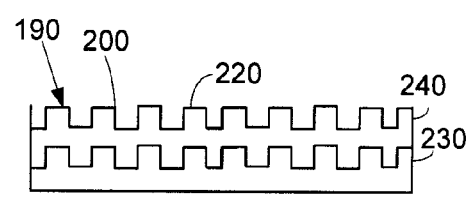
FIG. 4 is an alternative embodiment of a reflective diffuser as may be used with the NDIR sensor of FIG. 2.

The waveguide 150 may have one or more internal reflective surfaces 170 therein. In this example, a detector reflective surface 180 may be positioned above the infrared detector 120. The reflective surface 170 may be in the form of a reflective diffuser 190 instead of the specular reflective surface 55 described above. As opposed to such a smooth surface, the reflective diffuser 190 may include a non-specular or a textured surface 200. As is shown in exaggerated form in FIG. 3, the textured surface 200 may include a random pattern 210. Further, the textured surface 200 also may include a uniform or a precision pattern 220 as is shown in exaggerated form in FIG. 4. Any type of textured surface 200 may be used herein. Holographic patterns also may be used herein. Further, combinations of random patterns, precision patterns, holographic patterns, and the like may be used together herein.

If the waveguide 150 is injection molded thermoplastic component and the like, the injection mold may provide the textured surface 200 as part of the mold. The mold thus produces a textured component 230 with the textured surface 200. The surface properties largely may be controlled by the nature of the mold. The textured component 230 then may be coated or plated with a reflective coat 240 to produce the reflective diffuser 190. The reflective coating 240 may be metallic and the like. Many other manufacturing techniques may be used herein. For example, existing components may be textured via sandpaper and the like and then coated.

Figure 5:
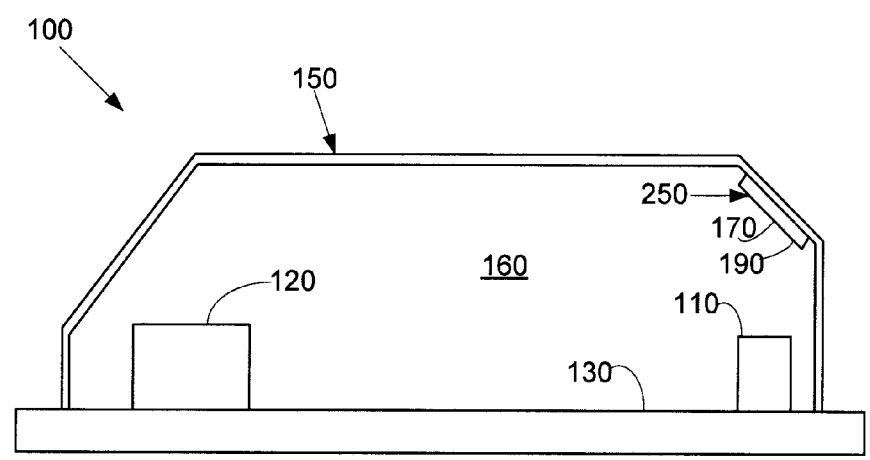
FIG. 5 is an alternative embodiment of an NDIR sensor.
Figure 6:
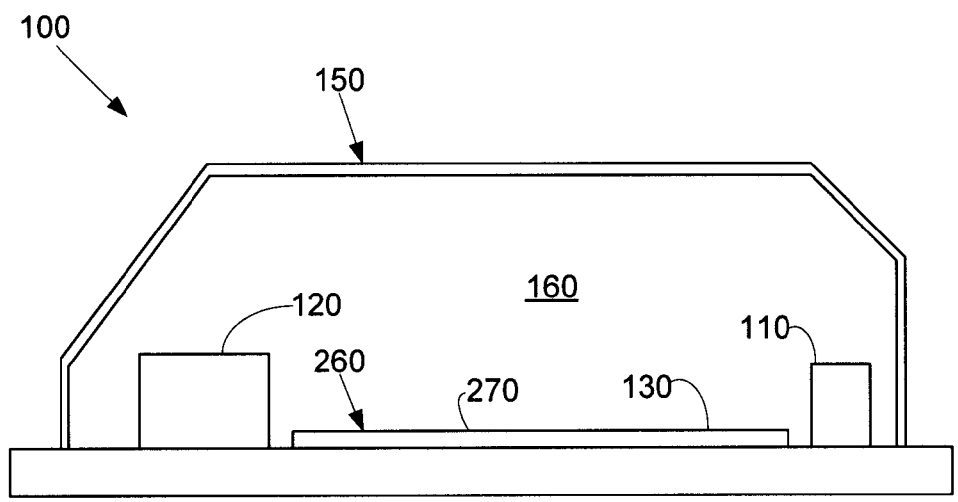
FIG. 6 is an alternative embodiment of an NDIR sensor.

The textured surface 200 of the reflective diffuser 190 is generally incorporated on a reflective surface 170 in the signal path where the majority of the infrared energy must pass. As such, the detector reflective surface 180 is shown in FIG. 2 adjacent to the infrared detector 120. Alternatively, FIG. 5 shows a source reflective surface 250 positioned above the infrared source 110. Multiple reflective surfaces 170 also may be used herein. Moreover, the printed circuit board 130 also may act as a reflective surface 170. In FIG. 6, the printed circuit board 130 may have a printed circuit board reflective surface 260. The printed circuit board reflective surface 260 may be electroplated with, for example, an electroless nickel immersion gold ("ENIG") surface 270. Such an ENIG surface 270 may be sufficiently textured so as to act as a reflective diffuser 190. Other types of surfaces 270 may be used. Other components and other configurations may be used herein.

In use, the NDIR gas sensor 100 with the reflective diffuser 190 induces scattering into the infrared signal pulses produced by the infrared source 110. Because the reflective energy is being diffused, the signals being reflected off of the textured surface 200 of the reflective diffuser 190 may have more of an average and homogeneous signal intensity distribution. The reflective diffuser 190 thus reduces overall mechanical sensitivity in the waveguide 50, the infrared source 110, and the infrared detector 120 such that the NDIR gas sensor 100 as a whole may have increased stability. The nature of the textured surface 200 of the reflective diffuser 190 may be optimized for different gases and intended uses.

Specifically, the NDIR gas sensor 100 described herein uses the textured surface 200 of the reflective diffuser 190 as a lambertian surface to induce scattering into the signal. This scattering thus optically averages the signal. The signal reflected off the reflective diffuser 190 has more of an average and homogeneous signal intensity distribution because the reflective energy therein is diffused. The more homogeneous signal intensity distribution thus results in reduced sensitivity to mechanical changes and therefore an increase in overall stability. As opposed to sensors with the specular surface 55 intended to reduce scattering described above, the NDIR gas sensor 100 herein purposefully induces such scattering for increased stability. Such an increase in stability may permit tighter accuracy specifications with lower costs. Other components and other configurations may be used herein.

Figure 7:
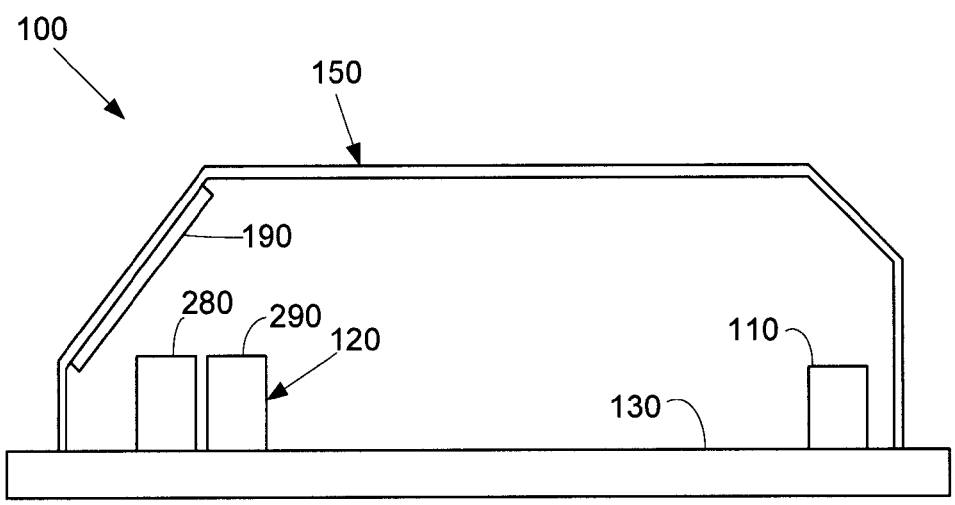
FIG. 7 is an alternative embodiment of an NDIR sensor.

The NDIR gas sensor 100 also may include multiple infrared detectors 120. In the example of FIG. 7, a first infrared detector 280 and a second infrared detector 290 may be used. Any number of infrared detectors 120 may be used herein. The infrared detectors 280, 290 may be in physically separated different locations. The signal reflected by the reflective diffuser 190 may result in similar energy presented to the detectors 280, 290. The reflective diffuser 190 thus averages the signals to allow both detectors 280, 290 to see similar intensity energy such that the sensor 100 may be less sensitive to mechanical changes.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

I claim:

1. A non-dispersive infrared gas sensor, comprising:
an infrared source;
an infrared detector; and
a waveguide extending about the infrared source and the infrared detector;
the waveguide comprising a reflective diffuser thereon, wherein the reflective diffuser comprises a printed circuit board reflective surface.

2. The non-dispersive infrared gas sensor of claim 1, wherein the waveguide defines a chamber.

3. The non-dispersive infrared gas sensor of claim 1, wherein the printed circuit board reflective surface comprises a textured surface.

4. The non-dispersive infrared gas sensor of claim 3, wherein the textured surface comprises a random pattern.

5. The non-dispersive infrared gas sensor of claim 3, wherein the textured surface comprises a precision pattern.

6. The non-dispersive infrared gas sensor of claim 3, wherein the reflective diffuser comprises a reflective coating thereon.

7. The non-dispersive infrared gas sensor of claim 1, wherein the printed circuit board reflective surface is formed on a textured thermoplastic component with a reflective metallic coating thereon.

8. The non-dispersive infrared gas sensor of claim 1, wherein the printed circuit board reflective surface comprises a detector reflective surface.

9. The non-dispersive infrared gas sensor of claim 1, wherein the printed circuit board reflective surface comprises a source reflective surface.

10. The non-dispersive infrared gas sensor of claim 1, wherein the printed circuit board reflective surface comprises an electroless nickel immersion gold surface.

11. The non-dispersive infrared gas sensor of claim 1, further comprising a plurality of infrared detectors.

12. The non-dispersive infrared gas sensor of claim 1, further comprising a plurality of infrared detectors spaced apart from each other.

13. The non-dispersive infrared gas sensor of claim 1, further comprising a microprocessor in communication with the infrared source and the infrared detector.

14. A method of measuring a concentration of a gas in a chamber, comprising:
    pulsing an infrared signal into the chamber;
    scattering the infrared signal off of a reflective diffuser, wherein the reflective diffuser comprises a printed circuit board reflective surface;
    receiving the scattered infrared signal at an infrared detector; and
    determining the intensity of the scattered infrared signal.

15. A non-dispersive infrared gas sensor, comprising:
    an infrared source;
    an infrared detector; and
    a waveguide extending about the infrared source and the infrared detector;
    the waveguide comprising a reflective diffuser with a textured printed circuit board reflective surface and a reflective coating thereon.

16. The non-dispersive infrared gas sensor of claim 15, wherein the textured printed circuit board reflective surface comprises a random pattern or a precision pattern.

17. The non-dispersive infrared gas sensor of claim 15, wherein the textured printed circuit board reflective surface comprises a detector reflective surface.

18. The non-dispersive infrared gas sensor of claim 15, wherein the textured printed circuit board reflective surface comprises a source reflective surface.

19. The non-dispersive infrared gas sensor of claim 15, wherein the textured printed circuit board reflective surface comprises an electroless nickel immersion gold surface.

\* \* \* \* \*